US007097824B2

(12) United States Patent
Sharma

(10) Patent No.: US 7,097,824 B2
(45) Date of Patent: *Aug. 29, 2006

(54) TUFTSIN METALLOPEPTIDE ANALOGS AND USES THEREOF

(75) Inventor: Shubh D. Sharma, Plainsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 261 days.

This patent is subject to a terminal disclaimer.

(21) Appl. No.: 10/364,842

(22) Filed: Feb. 11, 2003

(65) Prior Publication Data

US 2003/0165427 A1   Sep. 4, 2003

Related U.S. Application Data

(60) Division of application No. 09/387,715, filed on Aug. 30, 1999, now Pat. No. 6,551,574, which is a continuation of application No. PCT/US99/05693, filed on Mar. 16, 1999, application No. 10/364,842, which is a continuation-in-part of application No. 08/660,697, filed on Jun. 5, 1996, now Pat. No. 6,027,711, which is a continuation-in-part of application No. 08/476,652, filed on Jun. 7, 1995, now Pat. No. 5,891,418.

(60) Provisional application No. 60/112,235, filed on Dec. 14, 1998, provisional application No. 60/078,373, filed on Mar. 18, 1998.

(51) Int. Cl.
*A61K 51/00* (2006.01)
*A61M 36/14* (2006.01)

(52) U.S. Cl. ............... 424/1.69; 424/1.11; 424/1.65; 424/9.1; 530/330

(58) Field of Classification Search .............. 424/1.11, 424/1.65, 1.69, 9.1, 9.3, 9.4, 9.5, 9.6, 9.7, 424/9.8; 534/7, 10–16; 530/300, 324–330

See application file for complete search history.

(56) References Cited

U.S. PATENT DOCUMENTS

| 5,443,816 A | 8/1995 | Zamora et al. ............ 424/1.69 |
| 5,569,745 A * | 10/1996 | Goodbody et al. ......... 530/328 |
| 5,891,418 A * | 4/1999 | Sharma .................... 424/1.69 |
| 6,027,711 A * | 2/2000 | Sharma .................... 424/1.69 |
| 6,551,574 B1 * | 4/2003 | Sharma .................... 424/1.69 |
| 2003/0165427 A1 * | 9/2003 | Sharma .................... 424/1.69 |

OTHER PUBLICATIONS

Som et al., "Diagnosis of Osteomyelitis and Soft Tissue Infection Using a TC-99m Labeled Tuftsin-Analog Peptide", *The Journal of Nuclear Medicine*, vol. 38: 132P, No. 493.

* cited by examiner

*Primary Examiner*—Dameron L. Jones
(74) *Attorney, Agent, or Firm*—Stephen A. Slusher

(57) ABSTRACT

Tuftsin receptor-specific peptides, peptidomimetics and peptide-like constructs are provided, particularly for use in biological, pharmaceutical and radiopharmaceutical applications, in which the peptide, peptidomimetic or construct is conformationally fixed on complexation of the metal ion-binding portion thereof with a metal ion, resulting in a peptide, peptidomimetic or construct with increased affinity for the tuftsin receptor.

17 Claims, No Drawings

SEQUENCE LISTING

```
<160> NUMBER OF SEQ ID NOS: 55

<210> SEQ ID NO 1
<211> LENGTH: 4
<212> TYPE: PRT
<213> ORGANISM: homo sapiens

<400> SEQUENCE: 1

Thr Lys Pro Arg
 1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 2

Thr Lys Gly Cys Arg
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
```

```
<222> LOCATION: 2,4
<223> OTHER INFORMATION: D-amino acid

<400> SEQUENCE: 3

Thr Lys Gly His Arg
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 4

Pro Lys Gly Cys Arg
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 1
<223> OTHER INFORMATION: ACETYLATION
<220> FEATURE:
<221> NAME/KEY: modified residue
<222> LOCATION: 6,8
<223> OTHER INFORMATION: D-amino acid

<400> SEQUENCE: 5

His Asn Ala Lys Thr Lys Gly Cys Arg
 1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 1,3
<223> OTHER INFORMATION: D-amino acid

<400> SEQUENCE: 6

Lys Gly Cys Arg
 1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,3
<223> OTHER INFORMATION: D-amino acid
```

```
<400> SEQUENCE: 7

Thr Lys Ser Cys Arg
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3,6,8
<223> OTHER INFORMATION: D-amino acid

<400> SEQUENCE: 8

His Asn Ala Lys Thr Lys Gly Cys Arg
 1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 1
<223> OTHER INFORMATION: polyethylene glycol 5000 labeled
<220> FEATURE:
<221> NAME/KEY: modified residue
<222> LOCATION: 1,3
<223> OTHER INFORMATION: D-amino acid

<400> SEQUENCE: 9

Lys Gly Cys Arg
 1

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3,6,8
<223> OTHER INFORMATION: D-amino acid

<400> SEQUENCE: 10

His Asn Ala Lys Pro Lys Gly Cys Arg
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 11

Arg Arg Gly Cys Arg
```

```
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 12

Thr Arg Gly Cys Arg
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 13

Pro Arg Gly Cys Arg
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3,5
<223> OTHER INFORMATION: D-amino acid

<400> SEQUENCE: 14

Lys Thr Arg Gly Cys Arg
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,3
<223> OTHER INFORMATION: D-amino acid

<400> SEQUENCE: 15

Gly Lys Cys Arg
 1

<210> SEQ ID NO 16
<211> LENGTH: 4
<212> TYPE: PRT
<213> ORGANISM: Artificial Sequence
```

```
<220> FEATURE:
<223> OTHER INFORMATION: Description of Artificial Sequence: synthetic
      peptide
<220> FEATURE:
<221> NAME/KEY: modified residue
<222> LOCATION: 2,3
<223> OTHER INFORMATION: D-amino acid

<400> SEQUENCE: 16

Thr Lys Cys Arg
  1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 17

Thr Arg Gly Cys Lys
  1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 2
<223> OTHER INFORMATION: D-Orn
<220> FEATURE:
<221> NAME/KEY: modified residue
<222> LOCATION: 4
<223> OTHER INFORMATION: D-amino acid

<400> SEQUENCE: 18

Thr Xaa Gly Cys Arg
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,3,4
<223> OTHER INFORMATION: D-amino acid

<400> SEQUENCE: 19

Thr Arg Lys Cys Arg
  1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
```

```
<220> FEATURE:
<221> NAME/KEY: modified residue
<222> LOCATION: 2,3
<223> OTHER INFORMATION: D-amino acid

<400> SEQUENCE: 20

Gly Arg Cys Arg
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 1,2,3
<223> OTHER INFORMATION: D-amino acid

<400> SEQUENCE: 21

Arg Lys Cys Arg
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 1,3
<223> OTHER INFORMATION: D-amino acid

<400> SEQUENCE: 22

Arg Arg Cys Arg
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 1,3
<223> OTHER INFORMATION: D-amino acid

<400> SEQUENCE: 23

Arg Lys Cys Arg
 1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Thr Arg Arg Cys Arg
 1               5
```

```
<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 4
<223> OTHER INFORMATION: D-amino acid

<400> SEQUENCE: 25

Arg Gly Gly Cys Leu Arg
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 4
<223> OTHER INFORMATION: D-amino acid

<400> SEQUENCE: 26

Arg Thr Gly Cys Arg
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2
<223> OTHER INFORMATION: D-amino acid

<400> SEQUENCE: 27

Thr Arg Gly Cys Arg
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 4
<223> OTHER INFORMATION: D-amino acid

<400> SEQUENCE: 28

Arg Gly Gly Cys Arg
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
```

-continued

```
<220> FEATURE:
<221> NAME/KEY: modified residue
<222> LOCATION: 2,4
<223> OTHER INFORMATION: D-amino acid

<400> SEQUENCE: 29

Thr Gln Gly Cys Arg
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 4
<223> OTHER INFORMATION: D-amino acid

<400> SEQUENCE: 30

Thr Arg Gly Cys Arg
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 5
<223> OTHER INFORMATION: D-amino acid

<400> SEQUENCE: 31

Thr Arg Gly Gly Cys Arg
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 5
<223> OTHER INFORMATION: Orn
<220> FEATURE:
<221> NAME/KEY: modified residue
<222> LOCATION: 2,4
<223> OTHER INFORMATION: D-amino acid

<400> SEQUENCE: 32

Thr Arg Gly Cys Xaa
 1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 1
```

```
<223> OTHER INFORMATION: acetylation
<220> FEATURE:
<221> NAME/KEY: modified residue
<222> LOCATION: 1,3
<223> OTHER INFORMATION: D-amino acid

<400> SEQUENCE: 33

Lys Gly Cys Arg
  1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 34

Thr Lys Lys Cys Arg
  1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3,5
<223> OTHER INFORMATION: D-amino acid

<400> SEQUENCE: 35

Lys Thr Arg Lys Cys Arg
  1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 36

Thr Lys Arg Cys Arg
  1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 4
<223> OTHER INFORMATION: D-amino acid

<400> SEQUENCE: 37
```

Thr Arg Arg Cys Arg
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 3
<223> OTHER INFORMATION: Orn
<220> FEATURE:
<221> NAME/KEY: modified residue
<222> LOCATION: 2,4
<223> OTHER INFORMATION: D-amino acid

<400> SEQUENCE: 38

Thr Lys Xaa Cys Arg
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3,4,5
<223> OTHER INFORMATION: D-amino acid

<400> SEQUENCE: 39

Lys Thr Arg Lys Cys Arg
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,3
<223> OTHER INFORMATION: D-amino acid

<400> SEQUENCE: 40

Thr Arg Arg Cys Arg
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3
<223> OTHER INFORMATION: D-amino acid

<400> SEQUENCE: 41

Thr Arg Lys Cys Arg
 1               5

```
<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3
<223> OTHER INFORMATION: D-amino acid

<400> SEQUENCE: 42

Thr Lys Lys Cys Arg
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 43

Thr Arg Gly Cys Arg
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2
<223> OTHER INFORMATION: D-amino acid

<400> SEQUENCE: 44

Thr Arg Gly Cys Arg
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 4
<223> OTHER INFORMATION: D-amino acid

<400> SEQUENCE: 45

Thr Arg Gly Cys Arg
1               5

<210> SEQ ID NO 46
<211> LENGTH: 5
<212> TYPE: PRT
<213> ORGANISM: Artificial Sequence
<220> FEATURE:
```

```
<223> OTHER INFORMATION: Description of Artificial Sequence: synthetic
      peptide
<220> FEATURE:
<221> NAME/KEY: MOD_RES
<222> LOCATION: 5
<223> OTHER INFORMATION: Nle
<220> FEATURE:
<221> NAME/KEY: modified residue
<222> LOCATION: 2,4
<223> OTHER INFORMATION: D-amino acid

<400> SEQUENCE: 46

Thr Lys Gly Cys Xaa
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 47

Thr Ala Gly Cys Arg
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 48

Ala Lys Gly Cys Arg
 1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 3,5
<223> OTHER INFORMATION: D-amino acid

<400> SEQUENCE: 49

Lys Thr Lys Ser Cys Arg
 1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
```

```
<221> NAME/KEY: modified residue
<222> LOCATION: 3,5
<223> OTHER INFORMATION: D-amino acid

<400> SEQUENCE: 50

Lys Thr Arg Ser Cys Arg
 1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 6
<223> OTHER INFORMATION: Ahe
<220> FEATURE:
<221> NAME/KEY: modified residue
<222> LOCATION: 8,10
<223> OTHER INFORMATION: D-amino acid

<400> SEQUENCE: 51

Thr Lys Pro Pro Arg Xaa Thr Lys Gly Cys Arg
 1               5                  10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: 6
<223> OTHER INFORMATION: Ahe
<220> FEATURE:
<221> NAME/KEY: modified residue
<222> LOCATION: 2,4
<223> OTHER INFORMATION: D-amino acid

<400> SEQUENCE: 52

Thr Lys Gly Cys Arg Xaa Thr Lys Pro Pro Arg
 1               5                  10

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 53

Thr Lys Ser Cys Arg
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
```

```
<220> FEATURE:
<221> NAME/KEY: modified residue
<222> LOCATION: 2,4
<223> OTHER INFORMATION: D-amino acid

<400> SEQUENCE: 54

Thr Ser Ser Cys Arg
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: modified residue
<222> LOCATION: 2,4
<223> OTHER INFORMATION: D-amino acid

<400> SEQUENCE: 55

Thr Ser Ser Cys Ser
 1               5
```

TUFTSIN METALLOPEPTIDE ANALOGS AND USES THEREOF

CROSS-REFERENCE TO RELATED APPLICATIONS

This application is a division of U.S. patent application Ser. No. 09/387,715 filed Aug. 30, 1999, now U.S. Pat. No. 6,551,574, which is a continuation of PCT/US99/05693, filed Mar. 16, 1999, which claimed priority pursuant to 35 U.S.C. §119 of Provisional Patent Applications Ser. Nos. 60/078,373, filed Mar. 18, 1998 and 60/112,235 filed Dec. 14, 1998, the entire disclosures of which are hereby incorporated by reference.

This application is also a continuation-in-part application of U.S. patent application Ser. No. 08/660,697, entitled Structurally Determined Metallo-Constructs and Applications, filed Jun. 5, 1996 now U.S. Pat. No. 6,027,711, which in turn is a continuation-in-part application of U.S. patent application Ser. No. 08/476,652, entitled Peptide—Metal Ion Pharmaceutical Constructs and Applications, filed Jun. 7, 1995 now U.S. Pat. No. 5,891,418; the teachings of all of the foregoing applications are incorporated herein by reference as if set forth in full.

GOVERNMENT RIGHTS

This invention was made in part with government support under grant No. 1 R43 AI39343-01 from the U.S. Department of Health and Human Services. The U.S. Government retains certain rights in the subject invention.

FIELD OF THE INVENTION

The present invention relates to tuftsin receptor-specific peptide constructs which are conformationally fixed on complexation with a metal ion. The constructs, which may be peptidomimetic in nature, are useful in pharmaceutical and radiopharmaceutical applications.

Throughout this application, various publications are referred to, each of which is hereby incorporated by reference in its entirety into this application to more fully describe the state of the art to which the invention pertains.

BACKGROUND OF THE INVENTION

Tuftsin Receptor Peptide Construct. Ser. No. 08/660,697 teaches certain locally restricted peptides, in which the biological-function domain and metal-peptide backbone are combined, and the biological-function domain is specific for the tuftsin receptor found on polymorphonuclear (PMN) granulocytes, monocytes and macrophages.

Native tuftsin is a tetrapeptide of the sequence Thr-Lys-Pro-Arg (SEQ ID NO. 1), located as residues 289–292 of the Fc region of the heavy chain of leukokinin (a cytophilic γ-globulin). It is liberated by a combination of two cleavages. The C-terminal peptide bond is cleaved in the spleen by splenic enzyme and subsequent cleavage of the N-terminal peptide bond by enzyme leukokininase which occurs on the membranes of the granulocytes where it acts to stimulate phagocytosis. The tuftsin sequence stimulates macrophages and polymorphonuclear granulocytes towards phagocytosis. This sequence thus has a role in the immune system response for fighting infections and bacteria and other invasions. There are specific tuftsin receptors present on granulocytes and macrophages. The receptor density is approximately 50,000–100,000 per cell, with the receptor-tuftsin complex reported to internalize after binding. Thus a peptide specific for the tuftsin receptor may be used in the treatment of certain diseases, as is disclosed generally in U.S. Pat. No. 4,390,528 to V A Najjar and U.S. Pat. No. 5,028,593 to K Nishioka, the teachings of which are incorporated herein by reference.

The '697 application teaches a precursor peptide, incorporating both a metal ion-binding backbone and a tuftsin receptor-specific biological-function domain, which tuftsin receptor-specific domain is biologically active only on labeling or complexing the metal ion-binding backbone with a metal ion, of the following general formula:

$R_1$-Aaa-Bbb-Ccc-Ddd-Eee-$R_2$

Where:
Aaa=L- or D-configuration residue selected from Thr, Cys, Pen, Pro, or Ser and corresponding des-amino derivatives.
Bbb=L- or D-configuration residue with a positively charged side chain, and containing an N for metal ion complexation, such as Arg, Lys, Orn, homoArg, S-(2-aminoethyl)Cys, O-(2-aminoethyl)Ser and other similar basic amino acids, and derivatives thereof
Ccc=L- or D-configuration residue with an un-charged side chain, and containing an N for metal ion complexation, such as Gly, Ala, Aib, Val, Nle, Leu and similar amino acids with un-charged side chains.
Ddd=L- or D-configuration residue, providing an S, and preferably an S and N, for metal ion complexation, or alternatively two Ns for metal ion complexation, such as Cys, HomoCys, Pen, His and other synthetic or derivatized amino acids.
Eee=L- or D-configuration residue with a positively charged side chain, such as L- or D-isomers of Arg, Lys, Orn, homoArg, S-(2-aminoethyl)Cys, O-(2-aminoethyl)Ser and other similar basic amino acids, and their corresponding des-carboxyl derivatives. A similar aliphatic or aromatic chain with a basic functional group can also be substituted.
$R_1$=H, alkyl, aryl, alkylcarbonyl, arylcarbonyl, alkyloxycarbonyl, aryloxycarbonyl, or a polymer such as PEG, PVA, or polyamino acid, attached directly or through a carbonyl group. $R_1$ does not exist if Aaa is a des-amino amino acid.
$R_2$=amide, substituted amide, ester, or a polymer such as PEG, PVA, or polyamino acid. $R_2$ does not exist if Eee is a des-carboxyl amino acid.

One representative peptide from this series was the sequence Thr-D-Lys-Gly-D-Cys-Arg (SEQ ID NO. 2). This peptide displayed very high affinity ($K_D$=1–5 nM) for human leukocytes after its binding to reduced TcO[V]. When complexed to radioactive $^{99m}$TcO[V], the peptide localizes to the site of inflammation or infection on i.v. administration. The affinity of the peptide which is not complexed to a metal ion is on the order of $K_D$=$10^{-4}$ M.

The structure of the Thr-D-Lys-Gly-D-Cys-Arg (SEQ ID NO. 2) peptide after binding to technetium is as follows:

The '697 application teaches that this peptide can similarly be labeled with Re, and that similar peptides can also be designed and synthesized using an $N_4$ metal ion-binding domain, such as Thr-D-Lys-Gly-D-His-Arg (SEQ ID NO.

3). Tuftsin receptor-specific peptides disclosed in '697 include Thr-D-Lys-Gly-D-Cys-Arg (SEQ ID NO.4), Thr-D-Lys-Gly-D-His-Arg (SEQ ID NO.3) and Pro-D-Lys-Gly-D-Cys-Arg (SEQ ID NO. 4).

The peptides taught in '697 may be complexed with a non-radioactive ionic form of rhenium or another suitable isotope, thereby creating a non-radioactive metallopeptide drug for the treatment of disease. Such peptides may also be radiolabeled with a diagnostic metal ion, such as $^{99m}$Tc, and used to determine sites of concentration of granulocytes and macrophages, such as infections and inflammations, or radiolabeled with a therapeutic metal ion, such as $^{186}$Re or $^{188}$Re, and used in the treatment of disease.

In addition, tuftin has analgesic and other central nervous system effects. See, e.g., Herman et al., "Central Effects of Tuftsin," in *Antineoplastic, Immunogenic and Other Effects of the Tetrapeptide Tuftsin: a Natural Macrophage Activator*, Najjar V A and Freidkin M, eds., New York Academy of Sciences, 1983 [hereinafter *Antineoplastic*], 156–163; Paradowski et al., "The Influence of Tuftsin on Blood Pressure in Animals," in *Antineoplastic*, 164–167; Fridkin and Najjar, *Crit. Rev. Biochem. Med. Biol.*, 24 (1989). Herein disclosed are novel peptides and peptidomimetics which are specific for the tuftsin receptor and may be used as an analgesic and in the treatment of various other central nervous system conditions.

SUMMARY OF THE INVENTION

Metallopeptides. The present invention provides tuftsin receptor-specific peptides which comprise a metal ion-binding backbone for complexing with a metal ion, the peptide further comprising a tuftsin receptor-specific biological-function domain, in which the tuftsin receptor-specific domain is conformationally constrained on complexing the metal ion-binding backbone with the metal ion. The metal ion-binding backbone includes two or more contiguous amino acids available for complexing with a metal ion, provided such that the peptide is specific for the tuftsin receptor on complexing the metal ion-binding backbone with a metal ion. The tuftsin receptor-specific domain may be sychnological or rhegnylogical.

The present invention encompasses manufactured peptides and pharmaceutically acceptable salts thereof which are characterized by having a metal ion-binding backbone with two or more contiguous amino acids available for complexing with a metal ion, and a tuftsin receptor-specific biological-function domain which is conformationally constrained on complexing the metal ion-binding backbone with a metal ion. In general, at least a portion of tile peptide is conformationally constrained in a secondary structure on complexing the metal ion-binding backbone with the metal ion. The peptide may have a conformationally constrained global structure on complexing the metal ion-binding backbone with the metal ion. The tuftsin receptor-specific domain of the peptide is substantially more potent on complexation of the metal ion-binding backbone with the metal ion. The peptide is also substantially more resistant to enzymatic degradation after complexing the metal ion-binding backbone with a metal ion.

Typically, the metal ion-blinding backbone is designed so that all of the valences of the metal ion are satisfied on complexation of the metal ion. In such instances, the metal ion-binding backbone may be a plurality of amino acids each containing at least one nitrogen, sulfur or oxygen atom available for complexing with the available valences of the metal ion. The metal ion-binding backbone also may include a derivatized amino acid or spacer sequence which contains at least one nitrogen, sulfur or oxygen atom available for complexing with the available valences of the metal ion.

The biological-function domain of the tuftsin receptor-specific metallopeptide constitutes a ligand capable of binding with a receptor. The affinity of the tuftsin analog peptide ligand for its receptor will generally be substantially higher when the metal ion-binding backbone is complexed with the metal ion than that of the uncomplexed tuftsin analog ligand.

The metal ion to be complexed may be selected from the group of elements consisting of iron, cobalt, nickel, copper, zinc, manganese, arsenic, selenium, technetium, ruthenium, palladium, silver, cadmium, indium, antimony, rhenium, osmium, iridium, platinum, gold, mercury, thallium, lead, bismuth, polonium and astatine. For the peptides of this invention, a metal ion which has a coordination number of 4 and is able to complex with a tetradentate ligand is preferred. The isotope $^{99m}$Tc is particularly applicable for use in diagnostic imaging, and the isotopes $^{186}$Re and $^{188}$Re are preferred for therapeutic applications. Non-radioactive rhenium is particularly applicable for use in making non-radioactive metallopeptides.

Tuftsin Analogs. Peptides of this invention may be manufactured peptides and pharmaceutically acceptable salts thereof containing a metal ion-binding backbone including two or more contiguous amino acids available for complexing with a metal ion, and a biological-function domain specific for the tuftsin receptor, which tuftsin receptor-specific domain is conformationally constrained on complexing the metal ion-binding backbone with a metal ion.

The metal ion-binding backbone may be complexed with a gamma-emitting metal ion, and the peptide used for diagnostic imaging of sites of infection or inflammation. The peptide may also be used as an immunostimulatory agent, and may in such instances be complexed with a metal ion which is not radioactive. The foregoing peptides can be complexed with technetium-99m ($^{99m}$Tc) a gamma emitter useful in diagnostic radioimaging, or with either radioactive or non-radioactive isotopes of rhenium.

Accordingly, it is an object of this invention to devise, demonstrate and illustrate the preparation and use of highly specific conformationally restricted peptides, peptoids, related pseudopeptides, peptidomimetics and metallo-constructs formed by complexing sequences thereof to a desired metal ion so that the topography of the side chains in the resulting complex is a biologically active three-dimensional structure which binds to a tuftsin receptor.

Another object of this invention is to provide tuftsin receptor-specific peptide-metal ion complexes which have a higher level of stability and are less susceptible to proteolysis than either the uncomplexed peptide, or other peptides known in the art.

Another object of this invention is to provide for tuftsin receptor-specific peptide analogs which are not conformationally restricted in the absence of a metal ion, whereby the uncomplexed peptide analog is either inactive or demonstrates low potency, but which have high potency and concomitant conformational restriction on complexation with a metal ion.

Another object of this invention is to utilize metal complexation in a tuftsin receptor-specific peptide to cause specific regional conformational restrictions in the peptide so that the peptide conformation at the metal binding site is conformationally fixed on metal complexation.

Another object of this invention is to complex a tuftsin receptor-specific peptide to a metal ion so as to alter the in vivo biodistribution profile, rate and mode of clearance from the body, bioavailability and pharmacokinetics in mammals.

Another object of this invention is to provide tuftsin receptor-specific peptide-metal ion complexes which utilize stable non-radioactive metal ions, with the biological-function domain having specific tuftsin-like biological activity, such as for therapeutic treatment of disease.

Another object of this invention is to provide a molecule which, on complexing with a metal ion, includes a biological-function domain which is specific for tuftsin receptors, and which stimulates polymorphonuclear granulocytes, monocytes and macrophages towards phagocytosis, and may be used in diagnostic methods for abscess and infection imaging.

Another object of this invention is to provide a peptide-metal ion complex with a region specific for the tuftsin receptor on polymorphonuclear granulocytes and macrophages which increases the antigenic profile of antigens presented to such polymorphonuclear granulocytes and macrophages, thereby resulting in production of higher titer antibodies.

Another object of this invention is to develop a tuftsin receptor-specific peptide-metal ion complex which is an antagonist of tuftsin.

Another object of this invention is to develop a tuftsin receptor-specific peptide-metal ion complex which is an agonist of tuftsin.

Another object of this invention is to complex tuftsin receptor-specific peptides with radiometal ions for use in whole body imaging and radiotherapy so that the resulting peptide-metal ion complex is of higher affinity and specificity for the tuftsin receptor than the uncomplexed peptide molecule, and the resulting radiolabeled species is essentially carrier-free in terms of tuftsin receptor recognition.

Another object of this invention is to provide tuftsin receptor-specific peptide-metal ion complexes which can transit the gut-blood barrier, without significant enzymatic or peptidase degradation, and may be adapted for oral administration.

DETAILED DESCRIPTION OF THE INVENTION

Tuftsin receptor-specific peptide-metal ion complexes, and the precursor uncomplexed sequences, which include peptide, peptidomimetic, peptide-like and metallo-constructs, are provided for biological, pharmaceutical and radiopharmaceutical applications. In the tuftsin receptor-specific peptide-metal ion complexes the construct is conformationally fixed, with the tuftsin receptor-specific domain generally having increased affinity for its target on labeling the metal ion-binding backbone with a metal ion.

The peptide constructs of this invention can include a metal ion, and for embodiments in which the metal ion is used diagnostically or therapeutically, a medically useful metal ion. The metal ion is optionally radioactive, paramagnetic or superparamagnetic. The metal ion is an ionic form of an element selected from the group consisting of iron, cobalt, nickel, copper, zinc, manganese, arsenic, selenium, technetium, ruthenium, palladium, silver, cadmium, indium, antimony, rhenium, osmium, iridium, platinum, gold, mercury, thallium, lead, bismuth, polonium and astatine. The metal ion may also be an ionic radionuclide of indium, gold, silver, mercury, technetium, rhenium, tin, astatine or copper.

A radioactive medically useful metal ion may generate gamma rays, beta particles, or positrons which are converted into gamma rays on collision with electrons. The medically useful metal ion may be used in diagnostic imaging procedures including gamma scintigraphy, specific photon emission computerized tomography, or positron emission tomography. The medically useful metal ion may also be used diagnostically in magnetic resonance imaging. Medically useful metal ions may also be used therapeutically.

The type of medically useful metal ion depends on the specific medical application. Particularly useful metal ions include elements 25–30 (Mn, Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi.

The tuftsin receptor-specific domain of the peptide is a sequence of one or more amino acids which constitute a biologically active peptide sequence, exhibiting binding to the tuftsin receptor found on cells, tissues or organs. The tuftsin receptor-specific domain also includes any sequence which may be consecutive amino acids (sychnological) or may be non-consecutive amino acids (rhegnylogical), of one or more amino acids which forms a tuftsin receptor-specific ligand, which ligand is capable of forming a specific interaction with its acceptor or receptor. The term "receptor" is intended to include both acceptors and receptors. The peptide or the biological-function domain may optionally transmit a signal to the cells, tissues or other materials associated with the biological receptor after binding. The tuftsin receptor-specific domain may thus be either an agonist or antagonist, or a mixed agonist-antagonist. The tuftsin receptor-specific domain may also constitute a member of a "specific binding pair," wherein a specific binding pair comprises at least two different molecules, where one molecule has an area on the surface or in a cavity which specifically binds to a particular spatial and polar organization of the other molecule.

Radiopharmaceutical Applications. Products of this invention may be employed as radiopharmaceutical agents. For example, when labeled with gamma-emitting radioisotopes, such as $^{99m}$Tc, the products may be utilized as a diagnostic agent in nuclear medicine.

Products of this invention may also be used as therapeutic agents when labeled with alpha- or beta-emitting radioisotopes. For example, peptides labeled with alpha- or beta-emitting radioisotopes, such as rhenium-186 ($^{186}$Re) or rhenium-188 ($^{188}$Re), can be used for treating diseases.

For radiopharmaceutical applications, and other medical applications, the products of this invention offer significant advantages over conventional linear or single-chain peptide constructs. For example, it is known that conformationally constrained and dimeric peptides derived from hypervariable loop sequences of antibodies can bind antigens with an affinity up to 40-fold higher than that obtained with linear sequence peptides. The peptides of this invention are conformationally constrained on labeling with a metal ion, and have a higher affinity than that obtained with conventional linear sequences.

For radiopharmaceutical and other medical applications, the peptides of this invention may be delivered to a subject by any means known in the art. This includes intravenous injection, subcutaneous injection, administration through mucous membranes, oral administration, dermal administration, regional administration to an organ, cavity or region, and the like.

Non-Radiopharmaceutical Therapeutic Applications. The products of this invention may be used for therapeutic applications, and are particularly useful for peptide drugs in which a tuftsin receptor-specific biological-function domain is required. In these applications, the metal ion may serve only to conformationally constrain the peptide, or a portion thereof, or may itself be related to the therapeutic nature of the agent.

Specific Tuftsin Analogs. The peptides of Table 1 were synthesized by solid-phase peptide synthesis using Boc-chemistry, and were purified by HPLC to purity levels of 95% or higher and analyzed by electrospray mass spectrometry. For all products, the experimental and calculated molecular masses were identical.

Table 1. Primary Structure and Designation of Tuftsin Analogs, Shown Uncomplexed to a Metal Ion.

| SEQ ID NO. | Primary Structure |
|---|---|
| 2 | Thr-Lys-Gly-D-Cys-Arg |
| 5 | Ac-His-Asn-Ala-Lys-Thr-D-Lys-Gly-D-Cys-Arg |
| 6 | D-Lys-Gly-D-Cys-Arg |
| 7 | Thr-D-Lys-D-Ser-Cys-Arg |
| 8 | His-Asn-D-Ala-Lys-Thr-D-Lys-Gly-D-Cys-Arg |
| 9 | PEG$_{5000}$-D-Lys-Gly-D-Cys-Arg |
| 10 | His-Asn-D-Ala-Lys-Pro-D-Lys-Gly-D-Cys-Arg |
| 11 | Arg-D-Arg-Gly-D-Cys-Arg |
| 12 | Thr-D-Arg-Gly-D-Cys-Arg |
| 13 | Pro-D-Arg-Gly-D-Cys-Arg |
| 14 | Lys-Thr-D-Arg-Gly-D-Cys-Arg |
| 15 | Gly-D-Lys-D-Cys-Arg |
| 16 | Thr-D-Lys-D-Cys-Arg |
| 17 | Thr-D-Arg-Gly-D-Cys-Lys |
| 18 | Thr-D-Orn-Gly-D-Cys-Arg |
| 19 | Thr-D-Arg-D-Lys-D-Cys-Arg |
| 20 | Gly-D-Arg-D-Cys-Arg |
| 21 | D-Arg-D-Lys-D-Cys-Arg |
| 22 | D-Arg-Arg-D-Cys-Arg |
| 23 | D-Arg-Lys-D-Cys-Arg |
| 24 | Thr-Arg-Arg-Cys-Arg |
| 25 | Arg-Gly-Gly-D-Cys-Leu-Arg |
| 26 | Arg-Thr-Gly-D-Cys-Arg |
| 27 | Thr-D-Arg-Gly-Cys-Arg |
| 28 | Arg-Gly-Gly-D-Cys-Arg |
| 29 | Thr-D-Gln-Gly-D-Cys-Arg |
| 30 | Thr-Arg-Gly-D-Cys-Arg |
| 31 | Thr-Arg-Gly-Gly-D-Cys-Arg |
| 32 | Thr-D-Arg-Gly-D-Cys-Orn |
| 33 | Ac-D-Lys-Gly-D-Cys-Arg |
| 34 | Thr-D-Lys-Lys-D-Cys-Arg |
| 35 | Lys-Thr-D-Arg-Lys-D-Cys-Arg |
| 36 | Thr-D-Lys-Arg-D-Cys-Arg |
| 37 | Thr-Arg-Arg-D-Cys-Arg |
| 38 | Thr-D-Lys-Orn-D-Cys-Arg |

-continued

| SEQ ID NO. | Primary Structure |
|---|---|
| 39 | Lys-Thr-D-Arg-D-Lys-D-Cys-Arg |
| 40 | Thr-D-Arg-D-Arg-Cys-Arg |
| 41 | Thr-Arg-D-Lys-Cys-Arg |
| 42 | Thr-Lys-D-Lys-Cys-Arg |
| 43 | Thr-D-Arg-Gly-D-Cys-Arg |
| 44 | Thr-D-Arg-Gly-Cys-Arg |
| 45 | Thr-Arg-Gly-D-Cys-Arg |
| 46 | Thr-D-Lys-Gly-D-Cys-Nle |
| 47 | Thr-D-Ala-Gly-D-Cys-Arg |
| 48 | Ala-D-Lys-Gly-D-Cys-Arg |
| 49 | Lys-Thr-D-Lys-Ser-D-Cys-Arg |
| 50 | Lys-Thr-D-Arg-Ser-D-Cys-Arg |
| 51 | Thr-Lys-Pro-Pro-Arg-[NH-(CH$_2$)$_6$-CO]-Thr-D-Lys-Gly-D-Cys-Arg |
| 52 | Thr-D-Lys-Gly-D-Cys-Arg-[NH-(CH$_2$)$_6$-CO]-Thr-Lys-Pro-Pro-Arg |
| 53 | Thr-D-Lys-Ser-D-Cys-Arg |
| 54 | Thr-D-Ser-Ser-D-Cys-Arg |
| 55 | Thr-D-Ser-Ser-D-Cys-Ser |

The peptides of Table 1 are synthesized by any means known in the art, including those methods disclosed in '697, and are evaluated to determine their ability to complex $^{99m}$Tc. It was determined that each peptide complexed $^{99m}$Tc very effectively. Each peptide was labeled using an identical protocol. A 5–10 μg sample of the peptide taken in 0.001 N aq. HCl was mixed with 1–30 mCi of generator-eluted Na$^{99m}$TcO$_4$ in a 5 ml serum vial. The volume of the resulting mixture was adjusted to 600 μl using injectable saline. A 400 μl volume of a freshly prepared and nitrogen-purged phthalate-tartrate-Sn(II) buffer (40:10:1 mM) was then added to the vial under a nitrogen head space. The vial was immediately sealed and placed in a shielded boiling water bath. After 15 min. the vial was removed from the water bath and allowed to come to room temperature. A small amount of the sample (1–10 mCi) was analyzed by reverse-phase HPLC using a C-18 column (VYDAC, 250×4.8 mm, 10 micron particle size) with a 0–30% acetonitrile gradient in 0.1% aq. TFA completed in 30 min. at a flow rate of 1.5 ml/min. Radioelution profiles were generated using an in-line radioactivity detector (Beckman, Model 170). The Tc-peptide complexes were usually obtained as a mixture characterized by two HPLC peaks, presumptively due to syn- and anti-isomerism in the Tc=O core. The HPLC profiles for each of the $^{99m}$Tc-peptides showed a complete absence of free, uncomplexed $^{99m}$Tc (which elutes at 2.5–3 min. under the reverse-phase HPLC conditions described). The radiochemical purity, as calculated from the HPLC profiles, ranged from 90–97%.

The peptides of Table 1 may alternatively be labeled with $^{99m}$Tc by any of the means taught in '697, including use of stannous-tartrate-succinate buffer, stannous-EDTA-succinate buffer, stannous stabilized in glucoheptonate, or a stannous-borate-tartrate buffer, as well as other means of labeling with $^{99m}$Tc known in the art.

The peptides of Table 1 maybe complexed with non-radioactive metal ions, and rhenium is a preferred ion. Peptides in solution may be labeled by treatment with the rhenium transfer agent ReO[V]Cl$_3$(PPh$_3$)$_2$ in the presence of 1,8-Diazabicyclo[5,4,0] undec-7-ene as a base. Metal complexation in the presence of 1,8-Diazabicyclo[5,4,0]undec-7-ene as a base can conveniently be accomplished at ambient room temperature. In an alternative method of metal complexation a mild base, such as sodium acetate, can be used. In this case the peptide is taken in a suitable solvent, such as DMF, NMP, MeOH, DCM or a mixture thereof, and heated to 60–70° C. with the rhenium transfer agent ReO[V]Cl$_3$(PPh$_3$)$_2$ in the presence of sodium acetate for 15 minutes. Similarly, other bases such as triethylamine, ammonium hydroxide and so on, may be employed. Various mixtures of the solvents, also in combination with MeOH, and DCM, CHCl$_3$ and so on, may also be employed to yield optimized complexation results.

The peptides of Table 1 may be used as diagnostic imaging agents for localizing sites of infection or inflammation, particularly when labeled with $^{99m}$Tc, or as immunotherapeutic agents, particularly when labeled with radioactive isotopes of rhenium or complexed with non-radioactive isotopes of rhenium, all as described elsewhere herein and in '697.

The peptides of Table 1 have, on labeling with technetium, $^{99m}$Tc or a similar metal ion, a core configuration as shown below. In this configuration, each of $R_1$, $R_2$, $R_3$ and $R_4$, if provided, may be one or more amino acids as described herein, or may be other constructs as described herein. Amino acids, if provided, at $R_2$, $R_3$ and $R_4$, may form at least a part of the tuftsin receptor-specific biological-function domain. Amino acids with cationic side chains at two or more of $R_2$, $R_3$ or $R_4$ may form at least a part of the tuftsin receptor-specific biological-function domain. Peptides of this invention with amino acids having cationic side chains at $R_2$, $R_3$ and $R_4$ include SEQ ID NOS. 19, 21 22, 23 and 24. Peptides with cationic side chains at $R_2$ and $R_4$ include SEQ ID NOS. 2, 3, 4, 33, 7, 8, 10, 11, 12, 13, 14, 17, 18, 27, 30 and 32. Peptides with cationic side chains at $R_3$ and $R_4$ include SEQ ID NOS. 15, 16 and 20.

Peptides as disclosed herein may include either a D- or L-cysteine residue in the metal ion-binding domain and may incorporate a core sequence described by the formula:

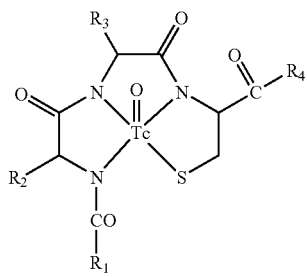

$R_2$-$R_3$-Cys-$R_4$ wherein $R_2$ is D- or L-Lys, Arg, Gly, Thr, Gln or Orn
$R_3$ is D- or L-Gly, Ser, Lys, Arg
Cys is D-Cys or L-Cys and
$R_4$ is D- or L-Arg, Lys, Leu or Orn The invention is further illustrated by the following non-limiting examples.

EXAMPLE 1

Kit Formulations for One Step Labeling with $^{99m}$Tc

The peptides SEQ ID NOS. 2 and 4 were formulated in lyophilized, one-step $^{99m}$Tc-labeling kit form. This was done to demonstrate that the peptides could be formulated in a commercially appropriate format. Fifty to 100 vials were prepared by making a bulk nitrogen-purged solution obtained by mixing the peptide (5–10 μg per vial) with 400 μl volume of a freshly prepared and nitrogen-purged phthalate-tartrate-Sn(II)] buffer (40:10:1 Mn, pH 6.0) per vial, all under sterile conditions. The resulting solution was filtered through 0.22 m low-binding filter and dispensed (400 μl per vial) in pyrogen-burned 5 ml serum vials. The vials were frozen, lyophilized and sealed under inert gas. The kits were stored at 4° C. until used. To label, 1–25 mCi of $^{99m}$Tc as Na$^{99m}$TcO$_4$ in 0.5–4 ml saline was added to the vial, and the vial placed in a boiling water bath for 15 min. The complexation efficiency was analyzed by RP-HPLC as described above. Lyophilized formulations yielded comparable results to those described above, ranging from 90–97% radiochemical purity.

EXAMPLE 2

SepPak Analysis of $^{99m}$Tc-Labeled Peptides

C-18 SepPak cartridges (Millipore Inc, Bedford, Mass.) were employed for quick analysis of labeling efficiency. This system provides three quantitative measures: (a) unbound $^{99m}$Tc in the form of $^{99m}$Tc—NaTcO$_4$ and $^{99m}$Tc-tartrate, (b) peptide-bound $^{99m}$Tc, and (c) $^{99m}$Tc-colloid. A freshly prepared $^{99m}$Tc-peptide complex (50–200 μCi in 10–200 μl) was loaded on a pre-conditioned cartridge. Pre-conditioning was done by successively eluting the cartridge with ethanol (10 ml) and 0.001 N aq. HCl (10 ml). The Tc-peptide-loaded cartridge was serially eluted with a 10 ml solution of 0.001 N aq HCl, 10% aq. EtOH, and 100% EtOH. All three eluants were counted for radioactivity in a dose calibrator, and the cartridge itself was also counted. The 0.001 N HCl eluant yielded the estimate of free, uncomplexed $^{99m}$Tc. The second eluant, 10% aq. EtOH, eluted all of the $^{99m}$Tc-bound peptide. The column radioactivity represented non-elutable $^{99m}$Tc-colloid. The radioactivity in these three fractions was computed in terms of percentages. The results with the peptides of Table 1 showed 1–3% free $^{99m}$Tc, 90–95% peptide-bound $^{99m}$Tc, and 2–5% $^{99m}$Tc-colloid. These results, together with HPLC profiles, indicated very high labeling efficiency for the peptides of Table 1.

EXAMPLE 3

Stability of $^{99m}$Tc-Peptide Complexes as Measured by Cysteine Challenge Studies The sulfhydryl group of Cys complexes to Tc with high affinity. Cys challenge studies therefore provide an estimate of the relative bond strength of Tc-peptide complexes. A constant amount of freshly labeled $^{99m}$Tc-peptide (10–100 μCi in 10–100 μl) was incubated with increasing amounts (0–100 mM) of Cys in PBS (pH 7.4) at 37° C. for one hour. Each sample was then analyzed either by HPLC or by the SepPak techniques described earlier. The amount of radioactivity not complexed to the peptide and the fraction remaining complexed to the peptide were computed. A graph of these values against Cys concentration was constructed to yield an IC$_{50}$ value (Cys concentration required to remove 50% of peptide-bound $^{99m}$Tc). The IC$_{50}$ values for peptide SEQ ID NOS. 2 and 4 ranged from 50–75 mM. Based on similar studies on various radiopharmaceuticals described in the literature, these values demonstrate very good stability for these Tc-peptide complexes. By comparison, the in vivo concentration of free sulfhydryl groups in serum is approximately 0.6 mM.

EXAMPLE 4

Metabolic Stability of $^{99m}$Tc-Peptides In Vivo in Rodents

The Tc-labeled peptides SEQ ID NOS. 2 through 32 were tested for in vivo metabolic stability in mice. Freshly labeled $^{99m}$Tc-peptide was injected through the tail vein in mice (50 μCi) or rats (100 μCi). The urine from these animals was collected after 30 and 120 min. The urine samples were centrifuged to remove any particulates. A urine sample containing 1–10 μCi (in 50–200 μl volume) was analyzed by RP-HPLC for the integrity of the labeled peptide. In all cases the $^{99m}$Tc-elution profile of the peptide in urine was similar to the original $^{99m}$Tc-peptide, revealing no change in the peptide as a result of injection into rodents. All the peptides were, therefore, metabolically stable and excreted intact in the urine. $^{99m}$Tc-labeled SEQ ID NO. 2 was administered both by subcutaneous injection and orally in mice, and the urine analysis by HPLC of these animals for both routes of administration also revealed 100% intact Tc-peptide, indicating oral absorption and complete in vivo metabolic stability of the peptide.

EXAMPLE 5

Metabolic Stability of $^{99m}$Tc-Peptides in Human Plasma In Vitro

The peptides SEQ ID NO. 4 and NH$_2$-Thr-D-Lys-Gly-D-Cys-Arg-COOH as described in '697 were assayed by incubating a sample of $^{99m}$Tc-peptide (100 µCi in 100 µl) with 100 µl of freshly prepared human plasma at 37° C. for 1–2 hrs. The sample was then injected into an RP-HPLC column as described above. Comparisons of the radio-elution profile with that of the original Tc-labeled peptide showed no change in the peptide, indicating metabolic stability of Tc-peptides in the presence of human plasma proteases.

EXAMPLE 6

Affinity of Tc-Labeled Peptides to Human Polymorphonuclear Granulocytes and Cultured HL-60 Cells The peptides SEQ ID NOS. 6 and 2 were used in direct saturation binding studies. Both peptides exhibited saturation binding kinetics. The assays were performed by both filtration and centrifugation techniques. Tc-labeled SEQ ID NO. 2 bound HL-60 and PMN granulocytes in saturable fashion with a $K_D$ value of 1–5 nM. Tc-labeled SEQ ID NO. 6 exhibited a $K_D$ value of 5–15 nM. In these experiments various amounts of the unlabeled peptides were used (10–100 µg) and labeled with a constant amount of $^{99m}$Tc and similar $K_D$ values were obtained. These results supported the hypothesis that Tc-labeled molecules are the only biologically relevant species and the presence of varied amounts of unlabeled peptides have no effect on receptor binding.

Competitive binding studies were performed to establish (a) binding of Tc-labeled peptide to the tuftsin receptor, (b) receptor affinity and (c) lack of receptor affinity of unlabeled peptides. $^{99m}$Tc-labeled peptide (a gamma emitter) was competed separately with increasing concentrations of $^{99}$Tc-labeled peptide (a weak beta emitter) and natural tuftsin. The IC$_{50}$ value for $^{99}$Tc-labeled SEQ ID NO. 2 was between 1–5 nM (similar to the values obtained for $^{99m}$Tc-labeled SEQ ID NO. 2 in saturation binding experiments). Natural tuftsin exhibited an IC$_{50}$ of approximately 100 nM. The unlabeled peptide (peptide uncomplexed to Tc) was 2000–3000 fold less potent than the Tc-labeled counterpart. Tc-labeled SEQ ID NO. 2 is up to 100-fold more potent than natural tuftsin, and may be the most potent tuftsin molecule known so far.

EXAMPLE 7

Stimulation of Phagocytic Activity of Granulocytes by $^{99m}$Tc-Peptides

Phagocytic assays using freshly harvested PMNs were performed using $^{99}$Tc-labeled or corresponding Re-labeled peptides according to the method described by Fridkin et al. (*Biochim Biophys Acta*, 1977, 496, 203–211). Metal ion-complexed SEQ ID NO. 2 was identified as a potent agonist in stimulating phagocytosis of heat inactivated yeast cells. The dose response curve was bell shaped as observed for other tuftsin peptides reported in the literature. Maximal effect was observed at 1–5 nM concentrations of the labeled peptide which paralleled its affinity in PMN binding experiments. Metal ion-complexed SEQ ID NO. 6 and SEQ ID NO. 4 were identified as potent antagonists in inhibiting tuftsin or Re-34 induced phagocytosis. SEQ ID NOS. 6,2 and 4 uncomplexed with a metal ion were not biologically relevant at the concentrations at which the metal ion complex species were potent.

EXAMPLE 8

Abscess Localization, Biodistribution, and Clearence Studies in Rodents

Normal mice and rats were used for biodistribution studies. In most of these studies the animals were injected 24 hrs prior to the study with turpentine (50 µl per mouse and 100 µl per rat) in the left thigh region to cause an experimentally induced sterile abscess. Mice (female, 25 g average weight) were injected with 50 µCi of the $^{99m}$Tc-peptide and rats (female, 230 g average weight) were given 100 µCi, all through tail veins. The biodistribution studies were performed at 30 and 120 min. time points. Animals were sacrificed and selected organs dissected and weighed, and associated radioactivity measured. The abscessed muscle as well as normal contralateral muscle was also excised. The data was computed using a computer program custom-designed for $^{99m}$Tc-labeled preparations. With all the $^{99m}$Tc-peptides no major accumulation of radioactivity in any organ was observed except for kidney and liver. Spleen and bone marrow in some cases also had accumulations slightly above the background levels established for other organs. The major excretion route for these peptides was through kidney and liver. As much as 75% of the radioactivity was excreted within the first 30 min. In the case of liver excretion, some radioactivity was found in the gut at the 120 min. time point. Table 2 (mouse model) and Table 3 (rat model) summarizes the results of the abscess uptake for various peptides studied during this study period. It is evident from these tables that peptides with high localization in the abscess as well with abscess to muscle ratios of as high as 10:1 were obtained.

TABLE 2

Abscess localization of the $^{99m}$Tc-peptide in mice model. Percent injected dose in whole blood and abscessed muscle is shown. Also shown are the ratios of the abscess (Ab) to blood (Bl) and to normal muscle (Mu).

| | 30 Min. | | | | 120 Min. | | | |
| --- | --- | --- | --- | --- | --- | --- | --- | --- |
| $^{99m}$Tc-Peptide SEQ ID NOS. | Total Blood (% ID) | Abscess (% ID) | Ratio Ab:Bl | Ratio Ab:Mu | Total Blood (% ID) | Abscess (% ID) | Ratio Ab:Bl | Ratio Ab:Mu |
| 2 | 0.49 | 0.31 | 1.45 | 6.59 | 0.45 | 0.30 | 1.84 | 10.81 |
| 4 | 5.48 | 1.70 | 0.62 | 3.15 | 1.22 | 0.36 | 0.63 | 4.63 |
| 2 | 6.75 | 2.07 | 0.73 | 3.05 | 1.05 | 0.44 | 1.08 | 7.19 |

TABLE 2-continued

Abscess localization of the $^{99m}$Tc-peptide in mice model. Percent injected dose in whole blood and abscessed muscle is shown. Also shown are the ratios of the abscess (Ab) to blood (Bl) and to normal muscle (Mu).

| | 30 Min. | | | | 120 Min. | | | |
|---|---|---|---|---|---|---|---|---|
| $^{99m}$Tc-Peptide SEQ ID NOS. | Total Blood (% ID) | Abscess (% ID) | Ratio Ab:Bl | Ratio Ab:Mu | Total Blood (% ID) | Abscess (% ID) | Ratio Ab:Bl | Ratio Ab:Mu |
| 5 | 3.84 | 1.28 | 0.78 | 4.54 | 0.61 | 0.36 | 1.31 | 8.25 |
| 6 | 3.18 | 1.58 | 1.83 | 3.53 | 0.32 | 0.50 | 3.61 | 8.38 |
| 7 | 7.70 | 1.54 | 0.44 | 3.78 | 1.60 | 0.44 | 0.64 | 4.91 |
| 8 | 6.78 | 1.18 | 0.40 | 2.55 | 2.00 | 0.62 | 0.64 | 6.03 |
| 10 | 15.29 | 1.83 | 0.29 | 3.21 | 3.76 | 0.43 | 0.27 | 3.28 |
| 11 | 31.28 | 1.10 | 0.10 | 2.12 | 4.25 | 0.38 | 0.25 | 2.51 |
| 12 | 15.3 | 1.14 | 0.20 | 2.97 | 8.36 | 0.98 | 0.28 | 3.1 |
| 14 | 3.35 | 1.80 | 1.31 | 5.45 | 0.81 | 0.35 | 1.53 | 8.90 |
| 15 | 3.34 | 2.00 | 1.38 | 6.42 | 0.38 | 0.49 | 2.83 | 12.03 |
| 19 | 3.48 | 1.05 | 0.68 | 2.70 | 0.66 | 0.34 | 1.15 | 6.09 |
| 22 | 3.19 | 1.00 | 0.79 | 3.32 | 1.20 | 0.21 | 0.56 | 4.76 |
| 23 | 2.61 | 1.19 | 1.04 | 3.86 | 0.34 | 0.16 | 1.08 | 3.67 |
| 24 | 3.36 | 1.54 | 0.78 | 8.59 | 0.55 | 0.24 | 0.77 | 2.79 |

TABLE 3

Abscess localization of the $^{99m}$Tc-peptide in rat model. Percent injected dose in whole blood and abscessed muscle is shown. Also shown are the ratios of the abscess (Ab) to blood (Bl) and to normal muscle (Mu).

| | 30 Min. | | | | 120 Min. | | | |
|---|---|---|---|---|---|---|---|---|
| $^{99m}$Tc-Peptide SEQ ID NOS. | Total Blood (% ID) | Abscess (% ID) | Ratio Ab:Bl | Ratio Ab:Mu | Total Blood (% ID) | Abscess (% ID) | Ratio Ab:Bl | Ratio Ab:Mu |
| 2 | 4.70 | 0.21 | 0.56 | 3.04 | 0.37 | 0.04 | 1.35 | 4.876 |
| 6 | 8.06 | 0.35 | 0.79 | 3.51 | 0.96 | 0.12 | 2.22 | 10.48 |
| 7 | 6.19 | 0.21 | 0.57 | 2.76 | 2.95 | 0.04 | 0.60 | 4.35 |
| 12 | 4.15 | 0.18 | 0.56 | 3.66 | 1.34 | 0.07 | 0.63 | 4.84 |
| 13 | 5.71 | 0.34 | 0.81 | 3.82 | 0.62 | 0.09 | 1.95 | 7.07 |
| 14 | 6.58 | 0.36 | 0.77 | 5.47 | 1.11 | 0.12 | 1.45 | 9.05 |
| 15 | 5.50 | 0.24 | 0.82 | 4.02 | 0.77 | 0.06 | 1.23 | 7.09 |
| 16 | 4.61 | 0.28 | 0.75 | 4.15 | 0.57 | 0.05 | 1.09 | 5.86 |
| 17 | 6.51 | 0.27 | 0.68 | 4.25 | 0.98 | 0.08 | 1.31 | 9.77 |
| 18 | 6.44 | 0.26 | 0.69 | 4.20 | 0.84 | 0.10 | 1.53 | 9.13 |
| 20 | 5.29 | 0.28 | 0.87 | 3.61 | 0.96 | 0.08 | 1.48 | 9.18 |
| 21 | 5.29 | 0.24 | 0.84 | 4.28 | 0.87 | 0.06 | 1.36 | 6.45 |

EXAMPLE 9

Preparation of Analogs Conjugated to Higher Molecular Weight Molecules

The conjugation of high molecular weight carrier molecules, such as PEG, PVA, fatty acids and others, to the peptides of Table 1 is achieved either after the synthesis of the peptide or during the synthesis of the peptide. PEG of various molecular weights (100–8000) and mono-methoxy PEG of similar molecular weights may be used by activation with disuccinimide carbonate as taught by S. Zalipsky (*Bioconjugate Chemistry* 4:296–299, 1993). The activated PEG is then treated with the peptide taken in phosphate buffer (125 mM, pH 6.5) in presence of 1 mM HOBt. After 1 hour at room temperature, the reaction mixture is extracted several times with dichloromethane. The combined organic extract is washed with water and evaporated to dryness. The product is then precipitated by the addition of anhydrous ether, and purified by precipitation from an ethanol-ether system. Alternatively carrier molecules are attached to the peptide during its synthesis by solid-phase or solution-phase methods of peptide synthesis. The carrier molecules are attached either at the N-terminus or C-terminus, or at both termini.

SEQ ID NO. 9 was synthesized by solid phase methods of peptide synthesis using monoethoxy-PEG-carboxylate of an average molecular weight of 5,000 for N-terminal conjugation to the peptide at the final step of synthesis.

EXAMPLE 10

Imaging of Sites of Infection or Inflammation

Any of the tuftsin analogs of Table 1 are radiolabeled as described, and optionally by means of the lyophilized kit of Example 1 or modifications thereof, with between 5 and 20 mCi of $^{99m}$Tc. The peptides of this invention may be employed at a ratio of peptide to metal ion of as low as 2:1, and in some instances lower, and thus the minimum quantity of peptide is generally determined by the quantity of metal ion. Generally, the total amount of peptide for diagnostic imaging applications will be between about 1 and 10 µg. The labeled tuftsin analog is administered, by i.v. injection or orally, to patients suspected of having one or more sites of abscess, infection or inflammation, and periodic whole body scintigraphic images are obtained following administration to determine the localization of the radiolabeled peptide to the abscess, infection or inflammation site or sites. The effectiveness of the labeled peptide to image the site or sites of abscess, infection or inflammation is noted.

EXAMPLE 11

Therapeutic Treatment with Rhenium Labeled Analogs

Any of the tuftsin analogs of Table 1 are complexed with an ionic form of non-radioactive rhenium. In one method, any of the tuftsin analogs of Table 1 may be complexed with an ionic form of non-radioactived rhenium by treatment in solution with the rhenium transfer agent ReO[V]Cl$_3$(PPh$_3$)$_2$ in the presence of 1,8-Diazabicyclo[5,4,0] undec-7-ene as a base. Metal complexation in the presence of 1,8-Diazabicyclo[5,4,0]undec-7-ene as a base can conveniently be accomplished at ambient room temperature.

Following complexation, the metallopeptides may be conveniently stored by any means known in the art, including lyophilization, freezing or retention in solution at appropriate storage temperatures. Alternatively, and depending on the disease to be treated and the selected mode of administration, the metallopeptides may be compounded into a tablet, capsule, caplet, syrup or other similar oral administration formulation, or alternatively, may be compounded into any method or system employed for the administration of peptides and peptide-based drugs, including intravenous formulations, intramuscular formulations, aerosol formulations, transmucosal formulations, transdermal formulations, nasal absorption formulations, oral cavity absorption formulations and the like. Depending on the disease or condition to be treated, which may be any of various immune system disorders or other conditions for which an immunostimulatory agent is appropriate, or may be any condition for which an analgesic agent is appropriate, including various central nervous system conditions, an effective amount of the metallopeptide is administered on an appropriate schedule.

All of the foregoing examples are merely illustrative, and other equivalent embodiments are possible and contemplated as within the scope of the invention. Variations and modifications of the present invention will be obvious to those skilled in the art. It is intended that the appended claims encompass all such modifications and equivalents.

What is claimed is:

1. A peptide, or a pharmaceutically acceptable salt thereof, comprising the sequence Thr-Arg-Arg-Cys-Arg, which is specific for the tuftsin receptor upon complexing with a metal ion.

2. A pharmaceutically acceptable salt of the peptide of claim 1.

3. The peptide of claim 1, wherein the metal ion-binding backbone of the peptide is complexed with a metal ion.

4. The peptide of claim 3, wherein the metal ion is radioactive.

5. The peptide of claim 3, wherein the metal ion is an isotope selected from the group consisting of isotopes of technetium and rhenium.

6. The peptide of claim 3, wherein the peptide complexed with a metal ion is substantially resistant to enzymatic degradation.

7. The peptide of claim 1, wherein the affinity of the peptide for the tuftsin receptor is substantially higher when the metal ion-binding backbone is complexed with the metal ion than is the affinity of the peptide for the tuftsin receptor when the metal ion-binding backbone is not complexed with the metal ion.

8. The peptide of claim 1, wherein the peptide is conjugated to a pharmaceutically acceptable carrier.

9. A method of imaging a site of infection or inflammation in a mammal comprising administering a diagnostically effective amount of a composition comprising the peptide of claim 1 complexed with a diagnostically useful metal ion.

10. The method of claim 9 wherein the diagnostically useful metal ion is $^{99m}$Tc.

11. A manufactured peptide, or a pharmaceutically acceptable salt thereof, comprising the sequence Thr-Arg-Arg-Cys-Arg, which is specific for the tuftsin receptor upon complexing with a metal ion.

12. The peptide of claim 11, wherein the peptide is complexed with a metal ion.

13. The peptide of claim 12, wherein the metal ion is radioactive.

14. The peptide of claim 12, wherein the metal ion is an isotope selected from the group consisting of isotopes of technetium and rhenium.

15. The peptide of claim 12, wherein the peptide complexed with a metal ion is substantially resistant to enzymatic degradation.

16. The peptide of claim 11, wherein the affinity of the peptide for the tuftsin receptor is substantially higher when the metal ion-binding backbone is complexed with the metal ion than is the affinity of the peptide for the tuftsin receptor when the metal ion-binding backbone is not complexed with the metal ion.

17. The peptide of claim 11, wherein the peptide is conjugated to a pharmaceutically acceptable carrier.

* * * * *